(12) United States Patent
Lading

(10) Patent No.: US 8,690,785 B2
(45) Date of Patent: Apr. 8, 2014

(54) METHOD AND AN APPARATUS FOR DETERMINATION OF BLOOD PRESSURE

(75) Inventor: Lars Lading, Roskilde (DK)

(73) Assignee: Sense A/S, Gentofte (DK)

( * ) Notice: Subject to any disclaimer, the term of this patent is extended or adjusted under 35 U.S.C. 154(b) by 1031 days.

(21) Appl. No.: 11/993,612

(22) PCT Filed: Jun. 27, 2006

(86) PCT No.: PCT/DK2006/000378
§ 371 (c)(1),
(2), (4) Date: Apr. 2, 2008

(87) PCT Pub. No.: WO2007/000164
PCT Pub. Date: Jan. 4, 2007

(65) Prior Publication Data
US 2010/0137724 A1    Jun. 3, 2010

(30) Foreign Application Priority Data

Jun. 27, 2005 (DK) .............................. 2005 00953

(51) Int. Cl.
*A61B 5/02* (2006.01)

(52) U.S. Cl.
USPC ........................... 600/485; 600/488; 600/481

(58) Field of Classification Search
USPC .................. 600/485, 488, 490, 494
See application file for complete search history.

(56) References Cited

U.S. PATENT DOCUMENTS

| | | | |
|---|---|---|---|
| 4,269,193 A * | 5/1981 | Eckerle | 600/485 |
| 4,687,476 A * | 8/1987 | Pailin | 604/307 |
| 4,799,491 A * | 1/1989 | Eckerle | 600/485 |
| 5,199,438 A * | 4/1993 | Pearlman | 600/483 |
| 5,441,968 A | 8/1995 | Brandstrom et al. | |
| 5,647,369 A | 7/1997 | Petrucelli et al. | |
| 6,015,386 A | 1/2000 | Kensey et al. | |
| 6,015,387 A | 1/2000 | Schwartz et al. | |
| 6,206,835 B1 | 3/2001 | Spillman, Jr. et al. | |
| 6,375,620 B1 | 4/2002 | Oser et al. | |
| 6,409,674 B1 | 6/2002 | Brockway et al. | |
| 6,533,729 B1 | 3/2003 | Khair et al. | |

(Continued)

FOREIGN PATENT DOCUMENTS

| | | |
|---|---|---|
| EP | 0319160 | 6/1989 |
| JP | 2001275998 | 10/2001 |

(Continued)

OTHER PUBLICATIONS

Japanese Office Action dated Dec. 20, 2011.

*Primary Examiner* — Michael Kahelin
*Assistant Examiner* — Tho Tran
(74) *Attorney, Agent, or Firm* — Volentine & Whitt, PLLC

(57) ABSTRACT

A method and an apparatus for non-interfering blood pressure measurements, relates to an apparatus for continuously monitoring blood pressure for patients at home or at work. The apparatus includes an extra-corporal sensor for blood pressure determination with a flexible housing adapted to be attached to the body of a living being proximate to an artery, and an electronic circuit for wireless coupling to a remote transceiver in accordance with the blood pressure in the artery, the remote transceiver adapted for wireless coupling to the sensor for generation of a pressure signal in accordance with the blood pressure in the artery, and a processor connected to the remote transceiver for reception of the pressure signal and adapted to estimate systolic and diastolic pressure based on the signal.

35 Claims, 6 Drawing Sheets

(56) References Cited

U.S. PATENT DOCUMENTS

| | | |
|---|---|---|
| 6,554,773 B1 | 4/2003 | Nissilae et al. |
| 6,558,225 B1 | 5/2003 | Rehkemper et al. |
| 7,935,061 B1* | 5/2011 | Breed et al. .................. 600/485 |
| 2002/0059081 A1* | 5/2002 | Yasuda et al. ..................... 705/3 |
| 2002/0151816 A1 | 10/2002 | Rich et al. |
| 2003/0032993 A1 | 2/2003 | Mickle et al. |
| 2003/0060721 A1 | 3/2003 | Nakazawa et al. |
| 2004/0133092 A1 | 7/2004 | Kain |
| 2004/0193058 A1 | 9/2004 | Montegrande et al. |
| 2005/0015014 A1 | 1/2005 | Fonseca et al. |
| 2005/0119833 A1* | 6/2005 | Nanikashvili ................... 702/19 |
| 2006/0103506 A1* | 5/2006 | Rodgers et al. .............. 340/10.5 |
| 2007/0060812 A1 | 3/2007 | Harel et al. |
| 2009/0054866 A1* | 2/2009 | Teisen-Simony et al. .... 604/506 |

FOREIGN PATENT DOCUMENTS

| | | |
|---|---|---|
| JP | 2004049579 | 2/2004 |
| JP | 2004121866 | 4/2004 |
| JP | 2004350786 | 12/2004 |

* cited by examiner

METHOD AND AN APPARATUS FOR DETERMINATION OF BLOOD PRESSURE

CROSS REFERENCE TO RELATED APPLICATIONS

This application is the national phase under 35 U.S.C. 371 of PCT International Application No. PCT/DK2006/000378 which has an international filing date of Jun. 27, 2006, and also claims priority under 35 U.S.C. 119 to Danish application PA 2005 00953 filed on Jun. 27, 2005, which applications are hereby incorporated by reference in their entirety for all purposes as if fully set forth herein.

FIELD OF THE INVENTION

The present invention relates to a method and an apparatus for non-interfering blood pressure measurements. In particular, the invention relates to an apparatus for continuously monitoring blood pressure for patients at home or at work.

BACKGROUND OF THE INVENTION

Blood pressure can be measured in a number of ways, such as invasive pressure sensor, oscillometric, auscultatory and tonometric. These methods will inevitably affect the state of the patient. It has been reported that a considerable number of measurements performed at the office of a medical doctor or at a hospital are affected by the situation and may be quite erroneous compared to what would have been measured if the patient had not been affected by the medical environment. The variations of the blood pressure in relation to the activity of the patient may provide very important information in relation to diagnosis. Existing methods do not provide non-interfering recording of blood pressure during sleep or during physical activity. Existing systems with a minimum interference do require either electrical wired power connection or an internal battery. These facts impose limitations on the applicability of the system and may have undesirable environmental effects.

In U.S. Pat. No. 6,558,335, a wrist-mounted device is disclosed. The device is based on a conventional MEMS pressure sensor, and a local power supply in the form of a battery is required.

SUMMARY OF THE INVENTION

It is an object of the present invention to provide an apparatus that is suitable for continuous monitoring of blood pressure of a living being under normal living conditions.

According to the invention, the above-mentioned and other objects are fulfilled by an apparatus for determination of blood pressure, comprising an extra-corporal sensor for blood pressure determination with a flexible housing adapted to be attached to the body of a living being proximate to an artery, and an electronic circuit for wireless coupling to a remote transceiver in accordance with the blood pressure in the artery. The remote transceiver couples wirelessly to the sensor for generation of a signal in accordance with the blood pressure in the artery, and a processor is connected to the remote transceiver for reception of the signal and is adapted to estimate systolic and diastolic pressure based on the signal.

Preferably, the sensor is an extra-corporal sensor, i.e. adapted for use outside the protecting membranes of the body of a living being. Preferably, the sensor is a passive sensor, i.e. a sensor that does not require wired connection to a power supply, e.g. a battery, in order to operate correctly. Preferably, the sensor relies on passive components, such as capacitors, inductors, resistors, etc., for its operation.

In an embodiment of the present invention, the sensor is an active sensor, i.e. a sensor that is connected to a power supply, such as a battery or an energy harvesting device, e.g. a sun cell, etc.

The operating principles of the apparatus according to the present invention are based on the fact that the diameter of an artery varies in response to variations of the blood pressure. Since the artery wall is flexible, the diameter of the artery expands with increasing blood pressure. The housing of the sensor according to the invention is also flexible so that the geometry of the housing changes when the housing is attached to the body of the living being proximate the artery. Electronic circuitry in the housing is adapted to sense geometric variations of the housing and provide an electronic parameter variation in response to the geometric variation. Further, the remote transceiver is adapted to wirelessly determine the electronic parameter variation.

The housing may be a flexible laminated polymer structure, and preferably, the electronic circuit is embedded in the structure whereby a small sensor is provided at a low cost.

The wireless coupling may be an inductive coupling, a capacitive coupling, an electromagnetic coupling, such as radio coupling or optical coupling, or a combination thereof, etc. The sensor circuit may include an antenna.

Preferably, the electronic circuit is a resonant circuit comprising an inductor and a capacitor.

In an embodiment of the present invention, the electronic circuit comprises a capacitor, and the capacitance of the capacitor may vary with the diameter of the artery when the housing is attached to the body proximate to the artery.

In an embodiment of the present invention, the electronic circuit comprises an inductor, and the inductance of the inductor may vary with the diameter of the artery when the housing is attached to the body proximate to the artery.

In yet another embodiment, the damping of the resonant circuit varies with the diameter of the artery when the housing is attached to the body proximate to the artery.

Preferably, a surface of the housing has a surface adhesive for attaching the housing to the body in a way similar to application of a plaster.

Alternatively, a strap may fasten the housing.

In an embodiment of the present invention, the electronic circuit comprises a first capacitor having a first plate and a second plate. The first plate and the second plate may be connected to a third plate and a fourth plate, respectively, for forming capacitive couplings between the sensor and the transceiver. The first plate and the second plate may be connected to an inductor for forming inductive coupling between the sensor and the transceiver.

The transceiver comprises a circuit for determination of variations of the properties of the sensor.

In one embodiment of the present invention, the transceiver comprises a fifth plate and a sixth plate for forming capacitive couplings with corresponding third and fourth plates of the sensor. The fifth plate and the third plate forms a capacitive coupling and the sixth plate and the fourth plate forms a capacitive coupling, when the transceiver is positioned close to the sensor, e.g. around 1 cm or less, preferably less than 1 mm. The transceiver may comprise an astable oscillator, such as a multi-vibrator, e.g. a bi-stable multi-vibrator. Variation in the capacitance of the first capacitor of the sensor may lead to variation in the duty-cycle and/or the frequency of one or more output signals from the oscillator.

A metal sheet, e.g. a flexible metal sheet, may form a plate of a capacitor.

In an embodiment of the present invention, the transceiver comprises a circuit for determination of the resonant frequency of the resonant circuit of the sensor. Preferably, the transceiver comprises a transmitting antenna coupled as part of a tank circuit, which in turn is coupled to an oscillator. A signal is generated which oscillates at a frequency determined by the tank circuit modified by the wireless coupling of the resonant circuit of the sensor. This signal is applied to a frequency discriminator, which in turn provides a signal from which the resonant frequency of the sensor circuit is determined.

In one embodiment, the transceiver transmits a signal scanning the frequency across a predetermined spectrum. The current passing through the transmitting antenna has a peak at the resonant frequency of the sensor. The resonant frequency and bandwidth are thus determined from this peak in the current.

Alternatively or in combination, the transceiver may transmit an excitation signal from the antenna. The wireless coupling to the sensor with the resonant circuit modifies the impedance of the transmitting antenna. The resonant frequency and bandwidth of the sensor circuit is determined based on the change of the impedance of the transmitting antenna.

In yet another embodiment, the transceiver transmits a broadband signal or a signal with multiple frequencies so that a current is induced in the resonant circuit of the wirelessly coupled sensor. The current oscillates at the resonant frequency of the resonant circuit. The transceiver further has a receiving antenna that receives the transmitted signal minus the energy that is absorbed by the sensor. Thus, the power spectrum of the received signal will exhibit a minimum at the resonant frequency of the sensor. The resonant frequency and bandwidth of the sensor circuit are determined from this notch in the power spectrum of the received signal.

Transmitting two frequencies on either side of the peak frequency of the resonant circuit will make it possible to obtain an s-curve response by estimating the difference in the return signals at the two frequencies.

The impedance characteristics of the sensor may be estimated from the estimated spectral response. This complex spectral response, which gives both amplitude and phase, can be obtained by a Fourier Transform procedure and compensating for the spectral distribution of the transmitted signal. The moments of the spectrum, witch can give the total spectral power, the centre frequency, the spectral width and other spectral parameters, can be obtained from the derivatives of the correlation function corresponding to the spectrum. Estimates of the moments can be obtained by correlating different orders of temporal derivatives of the return signal.

The state of the sensor may also be detected with an impedance analyzer that can detect both the amplitude and phase characteristics of the sensor through a coupling device like a coil, a capacitor or an antenna.

The transceiver may be adapted to communicate, e.g. by wire or wirelessly, with a computer comprising a processor. The processor may be adapted to record a signal from the transceiver and perform the calculations for determination of pulse, systolic and diastolic blood pressure from the signal from the transceiver, temporal variations of these quantities as well as statistical properties, such as mean value, variance, correlation factors, etc., of these variations. Further, the computer may be adapted for displaying the calculated values and plotting values as a function of time. In a preferred embodiment, the transceiver communicates wirelessly with the computer, e.g. in accordance with the Bluetooth or the ZigBee standard, or any other suitable wireless protocol.

In an embodiment, the processor is located in the transceiver. The transceiver may further comprise a display for displaying determined values, e.g. the systolic and diastolic blood pressure and the pulse.

DETAILED DESCRIPTION OF PREFERRED EMBODIMENTS

Figure 1:
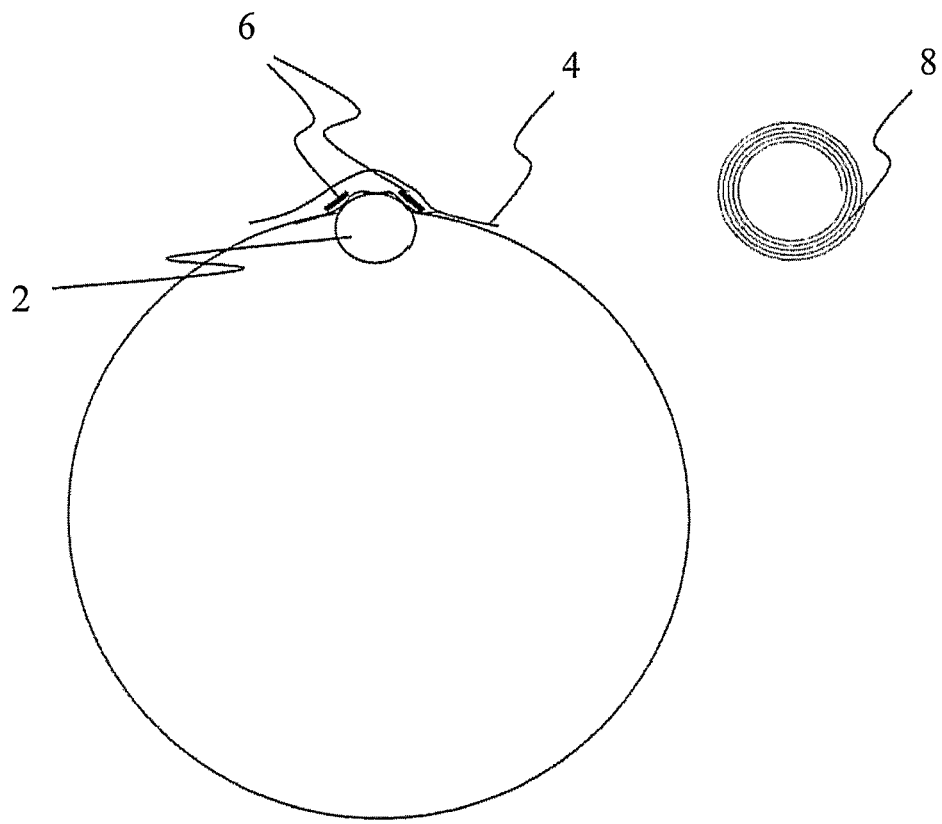
FIG. 1 schematically illustrates a cross-section of a sensor according to the present invention applied above an artery of a living being.

FIG. 1 schematically illustrates a cross-section of a sensor according to the present invention applied above an artery 2 of a living being. The sensor is supported by a flexible housing in the form of a flexible foil 4 that has an adhesive on its lower surface for attachment of the sensor to the skin surface immediately above the artery 2. The foil 4 supports mutually isolated metal sheets 6 forming a capacitor. The foil 4 is applied so that each of the metal sheets is positioned in close proximity to the artery 2. An inductor 8 is shown separately. The inductor 8 is printed into the foil 4. The capacitor and the inductor 8 are interconnected to form a resonant circuit and in the illustrated exemplary embodiment, the inductor value is fixed while the capacitor value varies with the diameter of the artery 2. An increased diameter of the artery 2 increases the distance between the metal sheets 6 decreasing the capacitor value.

In another embodiment, the inductor value varies with the diameter of the artery 2 while the capacitor value is fixed.

Figure 2:
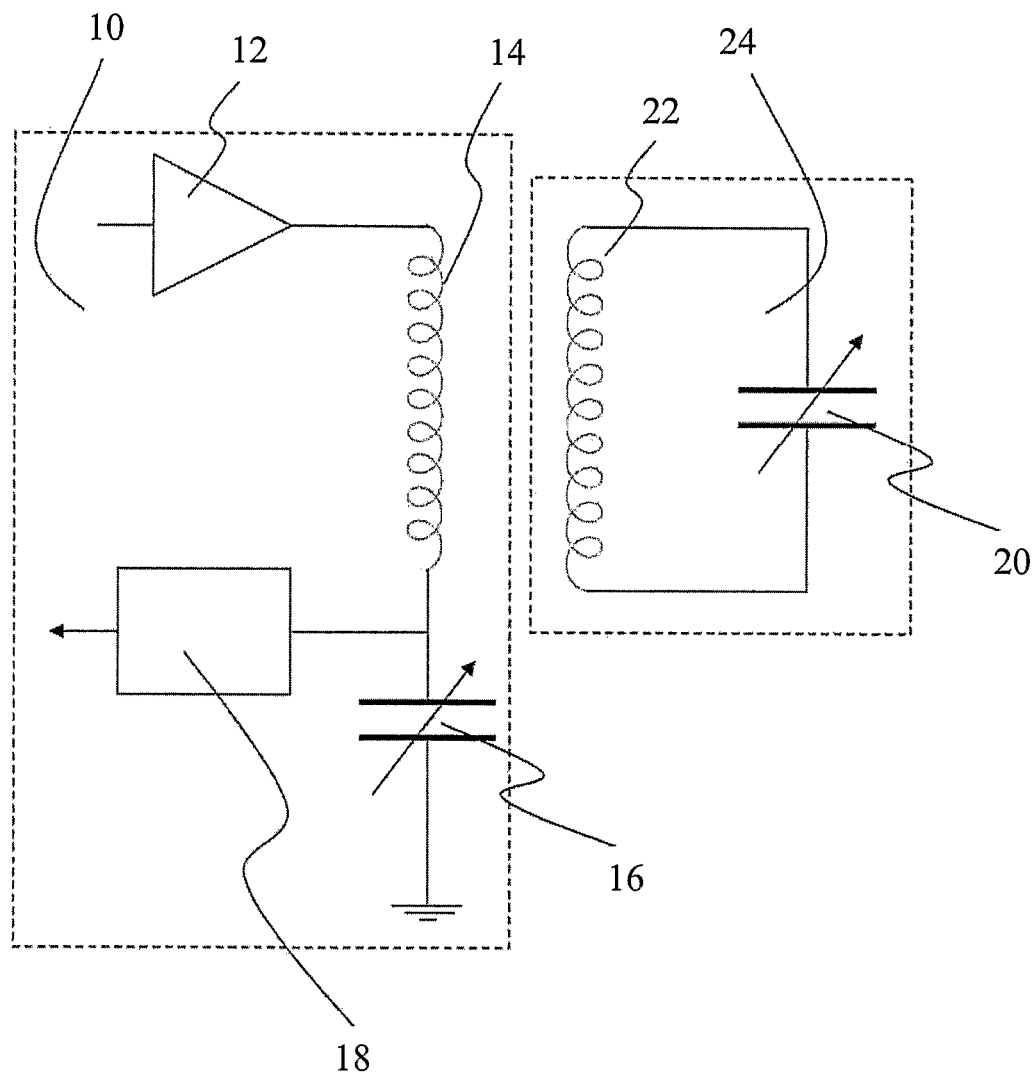
FIG. 2 is a blocked schematic of a sensor and a transceiver according to the present invention.

FIG. 2 is a blocked schematic of a sensor and a transceiver according to the present invention. The transceiver circuitry 10 comprises an amplifier 12, an inductor 14, a variable capacitor 16, and a frequency discriminator circuit 18. The inductor 14 and capacitor 16 forms a magnetically coupled resonant circuit together with the capacitor 20 and the inductor 22 of the sensor circuit 24. The resulting resonant frequency varies as a function of the value of capacitor 20 in the sensor circuit, which in turn varies in response to the blood pressure to be determined. The frequency discriminator circuit 18 detects the resulting resonance frequency and generates an electronic pressure signal with a value corresponding to the detected resonance frequency.

Figure 3:
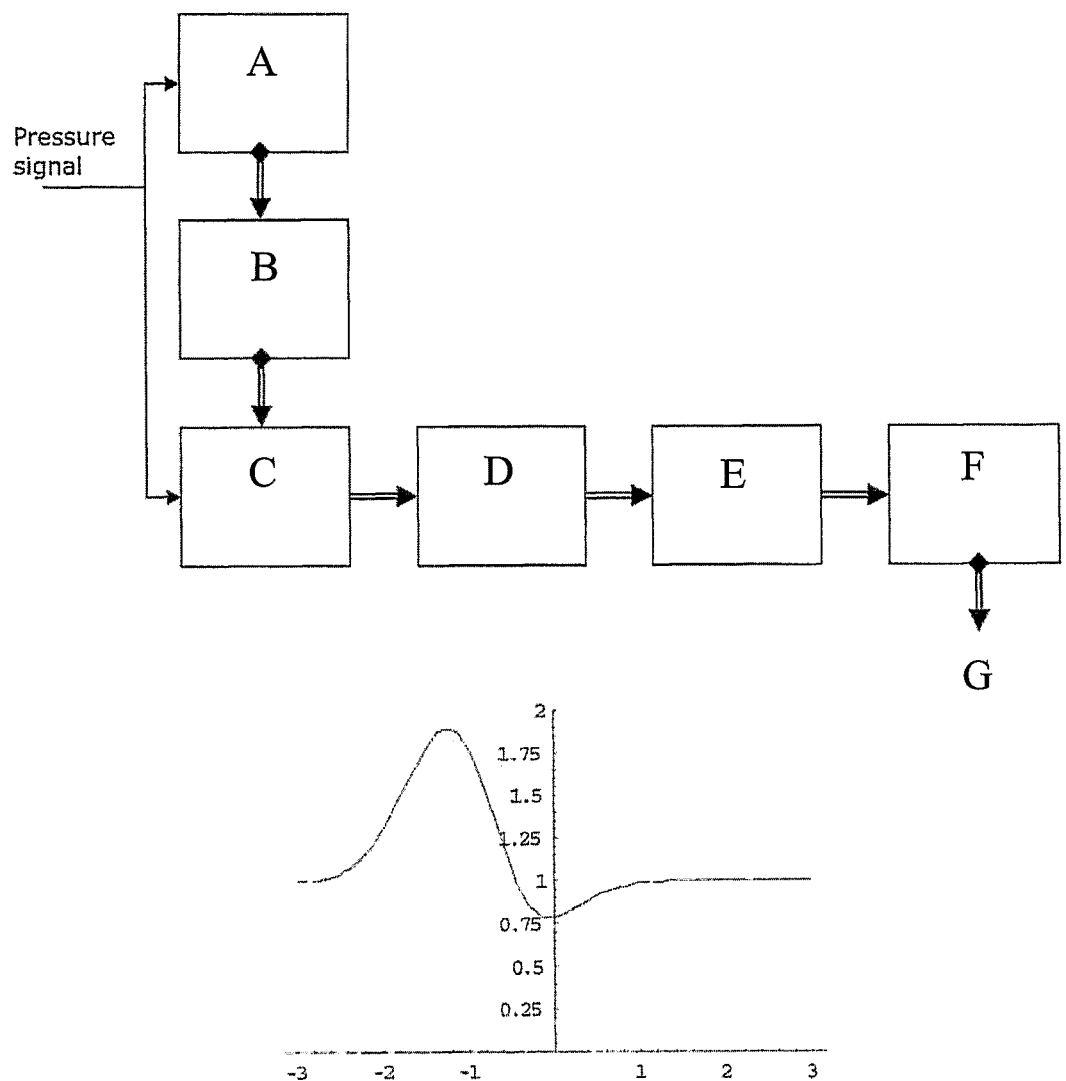
FIG. 3 is flowchart of an exemplary signal processing scheme according to the present invention, FIG. 4 schematically illustrates the various components of an embodiment of the present invention, FIG. 5 schematically illustrates a sensor and a transceiver according to the present invention, and FIG. 6 schematically illustrates an astable multi-vibrator comprised in a transceiver as illustrated in FIG. 5.

FIG. 3 is a flowchart of a preferred signal processing scheme according to the present invention. The pressure signal is determined at regular time intervals, and the determined values are fitted to an expected shape of the blood pressure as a function of time. The fitting is performed as a linear or non-linear least square fit. The fitting function is stretched to substantially match the temporal distance between consecutive heartbeats. The fitted curves are averaged over a period to be selected according to medical indication. For example, the fitted curves may be conditionally averaged over a period shorter than the characteristic time scale within which the blood pressure values may change. The conditional averaging is based on a good determination of the pulse. An averaged blood pressure curve is plotted at the lower part of FIG. 3. The averaging period is typically much larger than the time interval between consecutive pressure pulses. The maximum value and the minimum value of the averaged curve are determined for provision of the systolic and the diastolic blood pressure, respectively. Further, the average time difference between consecutive pulses is also determined for provision of the pulse. A calibration with a certified blood pressure measuring device is performed regularly.

In the illustrated embodiment, the signalling processing scheme thus comprises the steps:
A: Estimation of pulse spacing,
B: Reference pulse stretching,
C: Fitting,
D: Averaging,
E: Max. and Min. estimation, and
F: Weighting on the basis of a calibration.

The output G of the signal processing is estimates of systolic and diastolic pressure.

Figure 4:
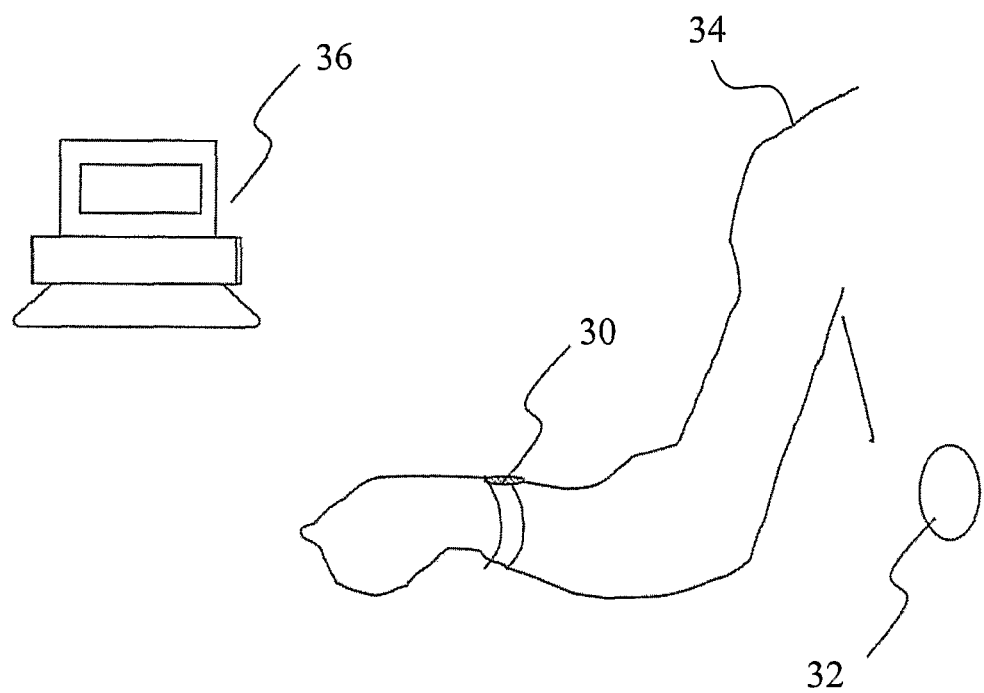

FIG. 4 schematically illustrates the various components of an embodiment of the present invention. The sensor 30 is typically mounted on the wrist of a patient. However, other positions may be selected as appropriate provided that an artery is close to the surface of the skin at the selected position. In the illustrated embodiment, the sensor 30 is a passive sensor that is fixed on the body above an artery. Preferably, the sensor has an adhesive surface for attaching the sensor to the body. The transceiver 32 is placed conveniently on the body of the patient 34 or adjacent the patient. The illustrated transceiver 32 communicates with a computer 36 with a processor that is adapted to record the pressure values and perform the calculations for determination of pulse, systolic and diastolic blood pressure. Further, the computer 36 is adapted for displaying the calculated values and plotting values as a function of time. In a preferred embodiment, the transceiver 32 communicates wirelessly with the computer, e.g. in accordance with the Bluetooth or the ZigBee standard.

In another embodiment, the processor is located in the transceiver. The transceiver may further comprise a display for displaying determined values, e.g. the systolic and diastolic blood pressure and the pulse.

Figure 5:
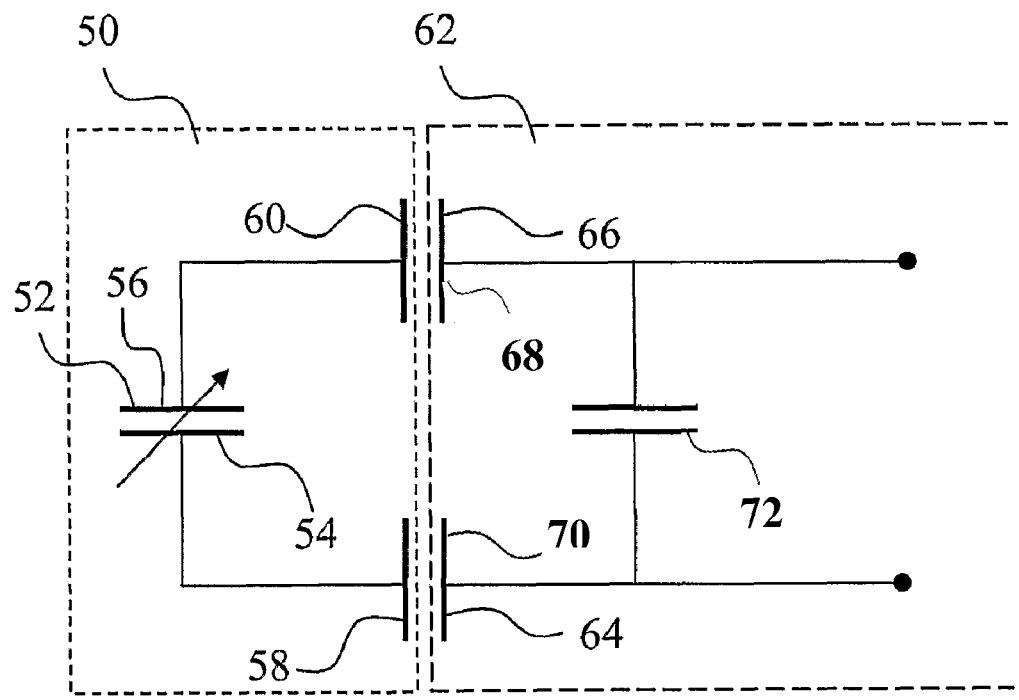

FIG. 5 is a blocked schematic of a sensor and a part of a transceiver according to the present invention illustrating a coupling between the sensor and the transceiver. The sensor 50 comprises a first capacitor 52 having two metal sheets forming a first plate 54 and a second plate 56, wherein the capacitance of the first capacitor 52 varies with the diameter of the artery when the housing is attached to the body proximate to the artery. The first plate 54 and the second plate 56 are connected to a third plate 58 and a fourth plate 60, respectively, for forming capacitive couplings between the sensor 50 and the transceiver 62. The transceiver 62 comprises a fifth plate 64 and a sixth plate 66 for forming capacitive couplings with corresponding third 58 and fourth 60 plates of the sensor. The capacitance of the second capacitor 68 and the third capacitor 70, respectively, is substantially constant during measurement. The second capacitor 68 and the third capacitor 70 may also be referred to as coupling capacitors. The transceiver may comprise a fourth capacitor 72. The transceiver 62 is adapted for measuring the variations in the first capacitor 52 whose capacitance varies as a function of time.

Figure 6:
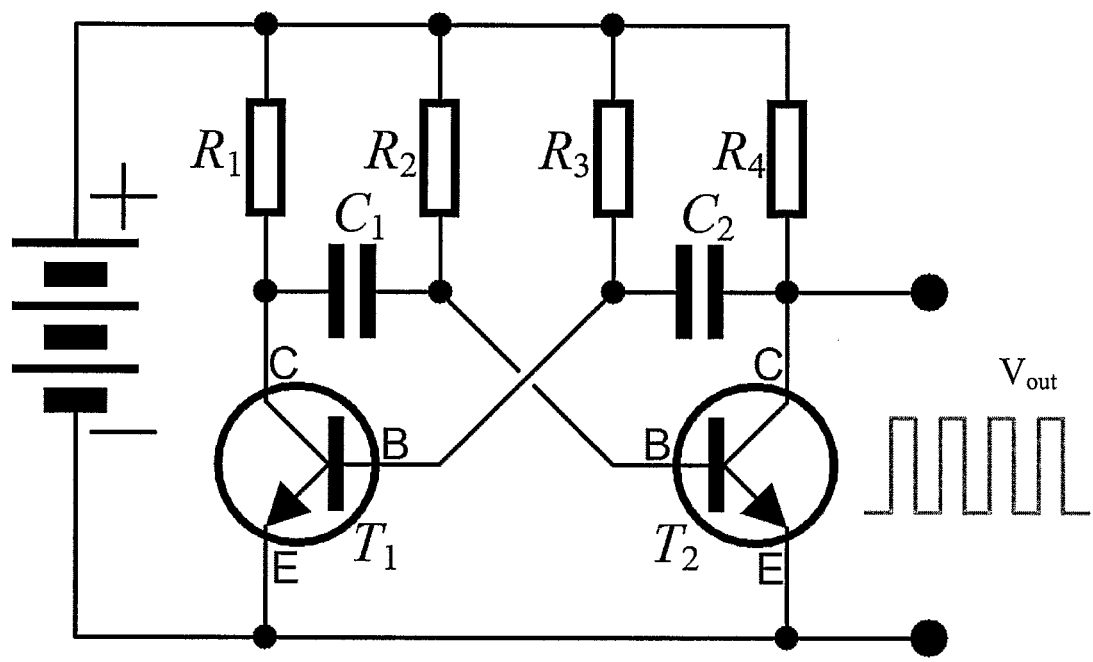

In an embodiment of the present invention, the transceiver 62 partly illustrated in FIG. 5 comprises an astable oscillator, which is schematically illustrated in FIG. 6. The capacitor $C_1$ indicates the varying capacitance of the circuit illustrated in FIG. 5. The transceiver may comprise a signal processing unit that is adapted to process the output signal $V_{out}$ from the oscillator. In an embodiment, the duty cycle of the output signal $V_{out}$ reflects the varying capacitance of the sensor, and the signal processing unit is adapted to determine the duty cycle of the output signal. Alternatively or in combination, the signal processing unit may be adapted to derive frequency information from the output signal $V_{out}$. The circuit of FIG. 5 may constitute or be a part of one of the capacitors $C_1$ and/or $C_2$.

The invention claimed is:

1. An apparatus for determination of blood pressure, comprising:
   a transceiver;
   at least one sensor for blood pressure determination with
      a flexible housing adapted to be attached to the body of a living being proximate to an artery,
      an electronic circuit for wireless coupling a pressure signal to the transceiver in accordance with the blood pressure in the artery,
      wherein the flexible housing is a flexible foil having an adhesive on a lower surface thereof and which supports each of mutually isolated metal sheets on the lower surface in such a way that when the flexible housing is attached to the body, the mutually isolated metal sheets form the plates of a capacitor with at least the artery as a dielectric between the plates, and
      an inductor placed into the flexible housing and connected to the mutually isolated metal sheets such that the capacitor, formed when the flexible housing is attached to the body, and the inductor are interconnected to form a resonant circuit as the electronic circuit,
   the transceiver adapted for wireless coupling to the electronic circuit of the at least one sensor for generation of the pressure signal in accordance with the blood pressure in the artery; and
   a processor connected to the transceiver for reception of the pressure signal and adapted to estimate systolic and diastolic pressure based on the signal.

2. The apparatus according to claim 1, wherein the at least one sensor is a passive sensor.

3. The apparatus according to claim 1, wherein the mutually isolated metal sheets of the capacitor are provided in the flexible housing in such a configuration that the field lines of said capacitor, when the at least one sensor is attached to the body, extend into the artery.

4. The apparatus according to claim 3, where the dielectric of said capacitor comprises tissue through which the field lines of said capacitor extend when extending into the artery.

5. The apparatus according to claim 1, wherein a capacitance of the capacitor varies with a diameter of the artery when the flexible housing is attached to the body proximate to the artery.

6. The apparatus according to claim 1, wherein the inductor has an inductor value and the capacitor has a capacitance value, and wherein said at least one sensor is adapted for sensing geometric changes of the flexible housing in such a way that when said flexible housing is attached to the body of the living being, proximate to the artery, the inductor value is fixed while the capacitor value varies with the diameter of the artery.

7. The apparatus according to claim 1, wherein the damping of the resonant circuit varies with a diameter of the artery when the flexible housing is attached to the body proximate to the artery.

8. The apparatus according to claim 1, wherein the adhesive is a surface adhesive for attaching the flexible housing to the body.

9. The apparatus according to claim 1, wherein the flexible housing comprises a flexible laminated polymer structure.

10. The apparatus according to claim 1, wherein the wireless coupling is a magnetic coupling or an electric coupling.

11. The apparatus according to claim 1, further comprising an impedance detector adapted to detect impedance changes.

12. The apparatus according to claim 1, wherein the processor is adapted to determine the pressure signal at regular time intervals by fitting an expected blood pressure function of time to the measured values.

13. The apparatus according to claim 1, wherein the processor is further adapted for pulse conditional averaging.

14. The apparatus according to claim 13, wherein the processor is adapted for estimating an impedance characteristics of the at least one sensor from an estimated spectral response, which gives both amplitude and phase, and is further adapted to perform the estimating by a Fourier Transform procedure and to thus compensate for the spectral distribution of the transmitted wireless pressure signal.

15. The apparatus according to claim 13, further comprising an impedance analyzer which is adapted to measuring the impedance characteristics of the at least one sensor through a coupling device comprising a coil, a capacitor or an antenna.

16. The apparatus according to claim 1, wherein the apparatus or the sensor is configured for extracorporeal use.

17. The apparatus according to claim 1, wherein the transceiver is a remote transceiver.

18. A blood pressure determination sensor comprising:
a transceiver;
a flexible housing having a lower surface with an adhesive thereon for external attachment to a body of a living being, proximate to an artery, wherein the flexible housing is a flexible foil, and the flexible housing supports each of mutually isolated metal sheets on the lower surface in such a way that when the flexible housing is attached to the body, the mutually isolated metal sheets form the plates of a capacitor with at least the artery as a dielectric between the plates; and
an inductor placed into the flexible housing and connected to the mutually isolated metal sheets such that the capacitor, formed when the flexible housing is attached to the body, and the inductor are interconnected to form a resonant circuit, forming an electronic circuit for wireless coupling to the transceiver for generation of a pressure signal in accordance with the blood pressure in the artery.

19. The blood pressure determination sensor according to claim 18, wherein the blood pressure determination sensor is adapted for being attached to the body extracorporeally on the skin.

20. The blood pressure determination sensor according to claim 18, wherein the mutually isolated metal sheets of the capacitor are provided in the flexible housing in such a configuration that the field lines of said capacitor, when the blood pressure determination sensor is attached to the body, extend into the artery.

21. The blood pressure determination sensor according to claim 20, where the dielectric of said capacitor comprises tissue through which the field lines of said capacitor extend while extending into the artery.

22. The blood pressure determination sensor according to claim 18, wherein the inductor has an inductor value and the capacitor has a capacitance value, and wherein said blood pressure determination sensor is adapted for sensing geometric changes of the flexible housing in such a way that when said flexible housing is attached to the body of the living being, proximate to the artery, the inductor value is fixed while the capacitor value varies with the diameter of said artery.

23. The blood pressure determination sensor according to claim 18, wherein the blood pressure determination sensor is a passive sensor.

24. The blood pressure determination sensor according to claim 18, wherein the damping of the resonant circuit varies with the diameter of the artery when the flexible housing is attached to the body proximate to the artery.

25. The blood pressure determination sensor according to claim 18, wherein the flexible housing comprises a flexible laminated polymer structure.

26. The blood pressure determination sensor according to claim 18, wherein the adhesive is a surface adhesive for attaching the flexible housing to the body.

27. A blood pressure determination method, comprising
providing a transceiver and a processor,
providing a blood pressure determination sensor with a flexible housing, wherein the flexible housing is a flexible foil having a lower surface with an adhesive thereon and which supports mutually isolated metal sheets on the lower surface,
attaching the blood pressure determination sensor by the adhesive to an exterior of a body of a living being, proximate to an artery, in such a way that when the flexible housing is attached to the body, said mutually isolated metal sheets form the plates of a capacitor with at least the artery as a dielectric between the plates,
an inductor being placed into the flexible housing and being connected to the mutually isolated metal sheets, such that said capacitor, formed when attaching said blood pressure determination sensor to said body, and the inductor are interconnected to form a resonant circuit, forming an electronic circuit for wireless coupling to the transceiver,
wireless coupling of said transceiver to the blood pressure determination sensor for generating a pressure signal in accordance with the blood pressure in the artery, and
connecting said processor to the transceiver and receiving the pressure signal and estimating systolic and diastolic pressure based on the pressure signal.

28. The method according to claim 27, wherein the mutually isolated metal sheets of the capacitor are provided in the housing in such a configuration that when the blood pressure determination sensor is attached to the body the field lines of said capacitor extend into the artery.

29. The method according to claim 28, where the dielectric of said capacitor comprises tissue through which the field lines of the capacitor extend while extending into the artery.

30. The method according to claim 27, wherein said blood pressure determination sensor senses geometric changes of the flexible housing when said flexible housing is attached to the body of the living being, proximate to the artery, the inductor value is fixed while the capacitor value varies with the diameter of said artery.

31. The method according to claim 27, wherein the damping of the resonant circuit varies with the diameter of the artery when the flexible housing is attached to the body proximate to the artery.

32. The method according to claim 27, wherein impedance characteristics of the blood pressure determination sensor are estimated from an estimated spectral response, which gives both amplitude and phase and is obtained by a Fourier Transform procedure and compensates for a spectral distribution of the transmitted wireless pressure signal.

33. The method according to claim 27, wherein the impedance characteristics of the blood pressure determination sensor is measured with an impedance analyzer through a coupling device comprising a coil, a capacitor or an antenna.

34. The method according to claim 27, where the blood pressure determination sensor is attached extracorporeally.

35. The method according to claim 27, where the capacitance of the capacitor varies with the diameter of the artery when the flexible housing is attached to the body proximate to the artery.

* * * * *